(12) United States Patent
Baecker et al.

(10) Patent No.: US 11,867,682 B2
(45) Date of Patent: Jan. 9, 2024

(54) SYSTEM AND METHOD FOR DETERMINING NATURAL HYDROCARBON CONCENTRATION UTILIZING ISOTOPE DATA

(71) Applicant: Baker Hughes Oilfield Operations LLC, Houston, TX (US)

(72) Inventors: Bastian Baecker, Falkensee (DE); Erik Lehne, Celle (DE); Svenja Erdmann, Isernhagen KB (DE); Salar Azizi, Hannover (DE)

(73) Assignee: Baker Hughes Oilfield Operations LLC, Houston, TX (US)

( * ) Notice: Subject to any disclaimer, the term of this patent is extended or adjusted under 35 U.S.C. 154(b) by 79 days.

(21) Appl. No.: 17/479,619

(22) Filed: Sep. 20, 2021

(65) Prior Publication Data

US 2022/0091090 A1    Mar. 24, 2022

Related U.S. Application Data

(60) Provisional application No. 63/080,818, filed on Sep. 21, 2020.

(51) Int. Cl.
*E21B 21/08* (2006.01)
*E21B 49/08* (2006.01)
*G01N 33/28* (2006.01)

(52) U.S. Cl.
CPC ......... *G01N 33/2823* (2013.01); *E21B 21/08* (2013.01); *E21B 49/088* (2013.01); *E21B 49/0875* (2020.05)

(58) Field of Classification Search
CPC .... E21B 21/08; E21B 49/0875; E21B 49/088; G01N 33/2823
See application file for complete search history.

(56) References Cited

U.S. PATENT DOCUMENTS

| 5,012,052 A | 4/1991 | Hayes |
| 5,525,799 A | 6/1996 | Andresen |

(Continued)

FOREIGN PATENT DOCUMENTS

| CA | 2660429 | 2/2008 |
| EP | 1 508 794 | 2/2005 |

(Continued)

OTHER PUBLICATIONS

D. Strapoc et al., "Artificial Alkenes and Alkanes Generated During Drilling: Evidence and Impact on Petroleum Exploration," 28th International Meeting on Organic Geochemisty, Sep. 17-22, 2017, Florence, Italy, European Association of Organic Geochemists, 2 pages.

(Continued)

*Primary Examiner* — Matthew R Buck
(74) *Attorney, Agent, or Firm* — Hogan Lovells US LLP

(57) ABSTRACT

A method for determining a hydrocarbon concentration from drilling fluid includes pumping the drilling fluid into a wellbore and circulating a sample of the drilling fluid uphole from the wellbore so that $\delta^{13}C$ isotopic signatures can be determined for one or more hydrocarbon components and for methane in the sample where the methane includes natural methane originating from the earth formation and artificially-produced methane caused by drill bit metamorphism (DBM). A processor is adapted to determine the concentration of the natural methane in the sample based in part on the $\delta^{13}C$ isotopic signatures which may be performed during the drilling of the wellbore.

20 Claims, 6 Drawing Sheets

(56) References Cited

U.S. PATENT DOCUMENTS

| | | | |
|---|---|---|---|
| 6,105,689 A | 8/2000 | McGuire | |
| 6,351,983 B1 | 3/2002 | Haas | |
| 6,389,878 B1 | 5/2002 | Zamfes | |
| 6,666,099 B2 | 12/2003 | Taylor | |
| 7,124,030 B2 * | 10/2006 | Ellis | G01N 33/241 702/9 |
| 7,174,254 B2 | 2/2007 | Ellis | |
| 7,290,607 B2 | 11/2007 | Tovar Depablos | |
| 7,323,341 B1 | 1/2008 | Jasper | |
| 7,421,881 B2 | 9/2008 | Nathan | |
| 7,465,426 B2 | 12/2008 | Kerherve | |
| 7,529,626 B1 | 5/2009 | Ellis | |
| 8,556,001 B2 | 10/2013 | Calleri | |
| 8,584,518 B2 | 11/2013 | Phillips | |
| 8,632,625 B2 | 1/2014 | DeGreeve | |
| 8,912,000 B2 | 12/2014 | Daniel | |
| 9,080,406 B2 | 7/2015 | Kelleher | |
| 9,238,948 B2 | 1/2016 | Gray | |
| 9,441,430 B2 | 9/2016 | Selman | |
| 9,671,381 B2 * | 6/2017 | Karoum | G01N 30/88 |
| 9,745,848 B2 | 8/2017 | Rowe | |
| 9,890,634 B2 | 2/2018 | Mitchell | |
| 11,320,414 B2 * | 5/2022 | Fayez | E21B 47/10 |
| 2004/0014223 A1 | 1/2004 | Audibert | |
| 2005/0082473 A1 | 4/2005 | Socki | |
| 2005/0150381 A1 | 7/2005 | Nathan | |
| 2005/0256646 A1 | 11/2005 | Ellis | |
| 2005/0256647 A1 | 11/2005 | Ellis | |
| 2008/0135236 A1 | 6/2008 | Schoell | |
| 2008/0147326 A1 | 6/2008 | Ellis | |
| 2008/0245960 A1 | 10/2008 | Csutak | |
| 2010/0031732 A1 | 2/2010 | Breviere | |
| 2010/0326651 A1 | 12/2010 | Pietrobon | |
| 2011/0094736 A1 | 4/2011 | Evrard | |
| 2011/0301866 A1 | 12/2011 | Holba | |
| 2011/0303464 A1 | 12/2011 | Lessi | |
| 2011/0308790 A1 | 12/2011 | Strapoc | |
| 2012/0134749 A1 | 5/2012 | Darrah | |
| 2013/0087698 A1 | 4/2013 | Pomerantz | |
| 2013/0233057 A1 | 9/2013 | Karoum | |
| 2013/0263647 A1 | 10/2013 | Barrett | |
| 2014/0130671 A1 | 5/2014 | DeGreeve | |
| 2015/0260703 A1 | 9/2015 | Mitchell | |
| 2016/0084023 A1 | 3/2016 | Calleri | |
| 2016/0153955 A1 * | 6/2016 | Strapoc | G01N 33/0047 702/24 |
| 2016/0160641 A1 | 6/2016 | Rowe | |
| 2016/0168985 A1 | 6/2016 | Betancourt-Pocaterra | |
| 2016/0356759 A1 | 12/2016 | Calleri | |
| 2017/0074094 A1 | 3/2017 | Rowe | |
| 2017/0122101 A1 | 5/2017 | Bright | |
| 2017/0176404 A1 | 6/2017 | Calleri | |
| 2017/0226851 A1 | 8/2017 | Hakami | |
| 2017/0259192 A1 | 9/2017 | Ochoa | |
| 2017/0268333 A1 | 9/2017 | Pickell | |
| 2017/0370167 A1 | 12/2017 | Aktas | |
| 2019/0368345 A1 | 12/2019 | Rowe | |
| 2021/0285927 A1 | 9/2021 | Baecker | |

FOREIGN PATENT DOCUMENTS

| | | |
|---|---|---|
| EP | 2 557 265 | 2/2013 |
| EP | 2 796 663 | 10/2014 |
| EP | 2 824 455 | 1/2015 |
| EP | 2 966 442 | 1/2016 |
| EP | 3 020 916 | 5/2016 |
| EP | 3 032 026 | 6/2016 |
| EP | 3 058 997 | 8/2016 |
| FR | 2815074 | 4/2002 |
| WO | 2004/104639 | 12/2004 |
| WO | 2006/114512 | 11/2006 |
| WO | 2008/017949 | 2/2008 |
| WO | 2009/059132 | 5/2009 |
| WO | 2010/081981 | 7/2010 |
| WO | 2011/159919 | 12/2011 |
| WO | 2013/021010 | 2/2013 |
| WO | 2013/052159 | 4/2013 |
| WO | 2013/071187 | 5/2013 |
| WO | 2015/006552 | 1/2015 |
| WO | 2015/023185 | 2/2015 |
| WO | 2015/047249 | 4/2015 |
| WO | 2015/171160 | 11/2015 |
| WO | 2016/093842 | 6/2016 |
| WO | 2016/126396 | 8/2016 |
| WO | 2017/139532 | 8/2017 |
| WO | 2017/165185 | 9/2017 |

OTHER PUBLICATIONS

D. Strapoc et al., "Deep biogenic methane and drilling-associated gas artifacts: Influence on gas-based characterization of petroleum fluids," The American Association of Petroleum Geologists, 2019, abstract only.

L. Ellis et al., "Mud gas isotope logging (MGIL) assists in oil and gas drilling operations," Oil & Gas Journal, May 26, 2003, vol. 101, No. 21, pp. 32-41.

A. V. Milkov et al., "Revised genetic diagrams for natural gases based on a global dataset of >20,000 samples," 2018, Organic Geochemistry, vol. 125, pp. 109-120.

M. Niemann et al., "Continuous Isotope Logging in Real Time While Drilling," Mar. 7-8, 2011, Petroleum Geology Conference and Exhibition, Kuala Lumpur Convention Center, Kuala Lumpur, Malaysia, 2 pages.

A. Piasecki et al, "Position-specific 13C distributions within propane from experiments and natural gas samples," 2018, Geochimica et Cosmochimica Acta, vol. 220, pp. 110-124.

M. Regan et al., "Near Real-Time Monitoring of PDC Bit Condition and Associated NPT Mitigation Using Online Alkene Detection," Aug. 27-29, 2018, IADC/Society of Petroleum Engineers Asia Pacific Drilling Technology Conference, Bangkok, Thailand, 11 pages.

L. M. Wenger et al., "Drill-Bit Metamorphism: Recognition and Impact on Show Evaluation," Oct. 4-7, 2009, 2009 SPE Annual Conference and Exhibition, New Orleans, LA, 9 pages.

Chung, H. M., J. R. Gormly, and R. M. Squires. Origin of gaseous hydrocarbons in subsurface environments: theoretical considerations of carbon isotope distribution. Chemical Geology 71.1-3 (1988): 97-104.

International Search Report and Written Opinion dated Dec. 28, 2021 in corresponding PCT Application No. PCT/US21/51171.

Wenger, L. et al., "Drill-Bit Metamorphism: Recognition and Impact on Show Evaluation," SPE Annual Technical Conference and Exhibition, New Orleans, Louisiana, Oct. 4, 2009, p. 1-9.

* cited by examiner

SYSTEM AND METHOD FOR DETERMINING NATURAL HYDROCARBON CONCENTRATION UTILIZING ISOTOPE DATA

CROSS-REFERENCES TO RELATED APPLICATIONS

This application is related to and claims the benefit of priority from U.S. Provisional Application No. 63/080,818, filed Sep. 21, 2020, and titled METHOD FOR UTILIZING NEAR REAL TIME ISOTOPE DATA TO CORRECT MUDGAS FOR ARTIFICIAL EFFECTS, the entire disclosure of which is incorporated by reference herein for all intents and purposes.

BACKGROUND

1. Field of Invention

This disclosure relates generally to oilfield equipment and more particularly to systems and methods for determining a concentration of a hydrocarbon in an underground or earth formation.

2. Description of the Prior Art

In drilling operations, mud gas logging may be useful for early assessment of reservoir type and quality. This allows for early decision making related to mitigation of risks and to plan for further operation management. Therefore, a correct gas composition derived from formations encountered during drilling operations is important to plan further strategies. However, mud gas logging and its associated analysis may be performed, in part, to address artificial effects, such as drill-bit-metamorphism (DBM). DBM can affect a gas component and its subsequent isotopic analysis, which then hampers a straightforward interpretation of mud gas analytical data.

SUMMARY OF THE DISCLOSURE

In at least one embodiment, a method to measure a concentration of natural methane in a sample of drilling fluid is disclosed. The method includes pumping the drilling fluid through a drill string into a wellbore. The sample of the drilling fluid is taken to a terranean surface. The sample includes a first hydrocarbon component, a second hydrocarbon component, and methane. The methane includes natural methane originating from the earth formation and artificially-produced methane caused by drill bit metamorphism (DBM). The method includes determining a $\delta13C$ isotopic signature of the first hydrocarbon component in the sample, determining a $\delta13C$ isotopic signature of the second hydrocarbon component in the sample, and determining a $\delta13C$ isotopic signature of the methane in the sample. Further, the method includes determining, using a processor, the concentration of the natural methane in the sample based in part on the $\delta13C$ isotopic signature of the first hydrocarbon component, the $\delta13C$ isotopic signature of the second hydrocarbon component, and the $\delta13C$ isotopic signature of the methane.

In at least another embodiment, a method to measure a concentration of natural methane in a sample of drilling fluid is disclosed. The method includes determining a $\delta13C$ isotopic signature of a first hydrocarbon component in the sample, a $\delta13C$ isotopic signature of a second hydrocarbon component in the sample, and a $\delta13C$ isotopic signature of methane in the sample. The methane includes natural methane originating from the earth formation and artificially-produced methane caused by drill bit metamorphism (DBM). The method includes determining, using a processor, the concentration of the natural methane in the sample based on the $\delta13C$ isotopic signature of the first hydrocarbon component, the $\delta13C$ isotopic signature of the second hydrocarbon component, and the $\delta13C$ isotopic signature of the methane.

In at least one other embodiment, a system to measure a natural concentration of methane in a sample of drilling fluid is disclosed. Such a system may include at least one processor and memory including instructions that, when executed by the at least one processor, cause the system to perform certain functions. A function performed by the system includes determining a $\delta13C$ isotopic signature of a first hydrocarbon component in the sample, a $\delta13C$ isotopic signature of a second hydrocarbon component in the sample, and a $\delta13C$ isotopic signature of methane in the sample. The methane includes natural methane originating from the earth formation and artificially-produced methane caused by drill bit metamorphism. A further function performed by the system includes determining the concentration of the natural methane in the sample based on the $\delta13C$ isotopic signature of the first hydrocarbon component, the $\delta13C$ isotopic signature of the second hydrocarbon component, and the $\delta13C$ isotopic signature of the methane.

BRIEF DESCRIPTION OF THE DRAWINGS

Various embodiments in accordance with the present disclosure will be described with reference to the drawings, as follows.

DETAILED DESCRIPTION

Figure 1:
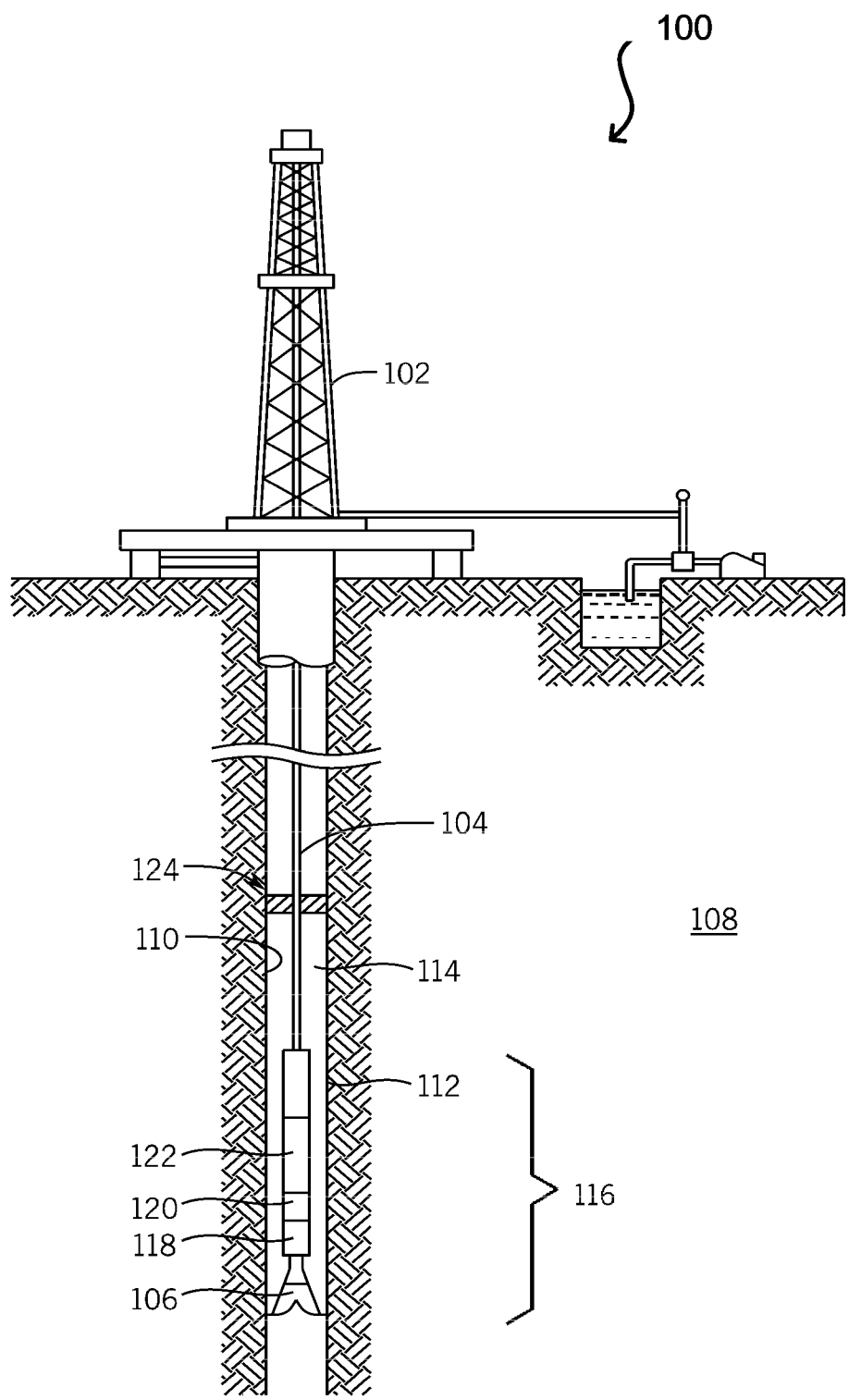
FIG. 1 illustrates an example downhole drilling system of at least one embodiment.

In the following description, various embodiments will be illustrated by way of example and not by way of limitation in the figures of the accompanying drawings. References to various embodiments in this disclosure are not necessarily to the same embodiment, and such references mean at least one. While specific implementations and other details are discussed, it is to be understood that this is done for illustrative purposes only. A person skilled in the relevant art will recognize that other components and configurations may be used without departing from the scope and spirit of the claimed subject matter.

When drilling into an underground or earth formation, drilling fluids, referred to as mud, are pumped into the formation to facilitate drilling. The mud lubricates the drill bit and prevents the drill bit from overheating. The mud can be circulated from a terranean surface, such as the earth's surface, to the drill bit and back, such that samples of the underground formation can enter the mud at the drill bit and be recovered at the surface as sample that can be analysed by measurement tools uphole of the drill bit.

The extracted drilling mud samples can be measured to determine characteristics of the formation. However, mud can include artificially generated components, such as those caused by drill bit metamorphism (DBM) asserted on drilling fluids, metamorphism on cuttings, or scavenger effects. Such mud components include (among possible others) alkenes, carbon monoxide, and, under circumstances, $H_2$ and He. These components hamper, under some circumstances, a straightforward interpretation of natural gas and oil occurring in the formation (such as, methane, ethane, and propane). DBM is particularly an issue in oil-based-mud (OBM).

Until recently, analysis relating to such straightforward interpretation of natural gas and oil occurring in the formation was not possible at a wellsite (having an underground formation) with enough accuracy and precision in data density (such as, in depth resolution) and with respect to certain compounds (such as, relating to chemical resolution of such compounds). Such data density and compound information were required to hold enough actionable information to make decisions pertaining to the wellsite. Particularly, in at least one embodiment, stable $^{13}C$ isotopes needed for analysis of an underground formation required several weeks to gather and was performed in a lab. Further, such lab requirements also included different lab equipment leading to slightly different isotope results than required to enable accuracy of the system and method herein. Measurements pertaining to isotope values for ethene and propene are required, along with one or more other hydrocarbons; but also, certain isotopes, such as pertaining to methane, ethane, and propane, were challenging to detect due to difficulties in securing peak separation.

A system and method herein are able to perform efficient natural gas correction at a wellsite, in an online stream mode representing a near real time (NRT) process. Surface logging analysis of the system and method herein allow for fast drilling fluid analyses at the well, drill, or rig site while drilling of the wellbore is ongoing (also referred to as an online stream mode). The identification of hydrocarbons and the determination of hydrocarbon properties at the rig site or elsewhere, while drilling is ongoing, may represent analysis performed at real time or NRT. An NRT analysis may take place within a few minutes after the sample is taken from the drilling fluid at the terranean surface. Further, an NRT analysis may take place within 10 minutes to 100 minutes after the sample is taken from the drilling mud and applied to a system to determine concentration and properties thereof.

Such an NRT process may be, therefore, performed in under 100 minutes, but under much lesser than 100 minutes time frame, from when a sample of the drilling fluid that was circulated uphole from the wellbore is entered for determination of isotopes therein to correcting a concentration of hydrocarbon using the isotopes. Particularly, stable $^{13}C$ isotopes are determined in NRT and gas components from the underground formation is therefore also determined in NRT at a wellsite or any location to which the sample is submitted.

As used herein, near real time can include measurements taken in real time and substantially close to real time. For example, near real time can include all results returned within a certain timeframe post-data collection, such as, without limitation, hundred minutes, thirty minutes, twenty minutes, ten minutes, five minutes, or some other time frame. In embodiments, C1 to C5 hydrocarbons are corrected for in under 35 seconds and up to C8 hydrocarbons are corrected for in under 180 seconds. In embodiments, data analysis occurs post-well too so that it is not necessarily limited to the well site. In at least one embodiment, the sample of the drilling fluid is taken from drilling fluid received uphole from the wellbore. The sample is entered in the present method or system, at a first time, for the determination of the $\delta^{13}C$ isotopic signatures. Correction, as detailed herein may be performed for the concentration of methane, at a second time. NRT determinations and corrections herein are so that a difference of the second time and the first time is 100 minutes or less.

In at least one embodiment, the system and method herein is able to use fast drilling operations, including using high rate of penetration (ROP) and high weight on bit (WOB), to cause temperatures associated with a drill bit to rise to higher values near the drill bit. Such higher values include temperatures that are greater than 600° C. At such temperatures, propene and some other hydrocarbons may form and are detectable by the system. Such hydrocarbons are detected as isotopes or are correlated with isotopes determined by the system. For example, stable $^{13}C$ isotopes may be provided especially for ethene and propene, which can indicate that drilling through steam reforming reactions within the mud is occurring. This may also be an indication that hydrocarbons are present in the mud gas from the underground formation.

Furthermore, heavier stable $\delta^{13}C$ isotopic signatures for ethane, ethene, propane, and propene may occur during drilling. These occurrences may reflect presence of DBM, in addition to the isomers of the compounds, for example, presence of iC4, nC4 compounds in the underground formation. Still further, an abundance of $CO_2$ and $H_2S$ produced from the mud gas and detected in circulated drilling fluid samples (especially when using diamond bits in anhydrite/gypsum/dolomite underground formation) may be measured and identified using isotope values as well.

In at least one embodiment, using stable $^{13}C$ and other isotopes, the method and system herein provides an efficient natural gas correction system that may be implemented at a wellsite in an online stream mode, in near real time (NRT). For example, a set of stable $^{13}C$ and other isotopes that are determined in NRT may be used to correct concentrations determined or measured for one or more hydrocarbons in a sample. As heavier demands are placed on drilling operations at least as to speed of operations, such demands can now be addressed by data driven justifications using the NRT information generated in the method and system herein. For example, such a method and a system may be able to address non-productive time (NPT) or invisible lost time (ILT) that is more apparent with the demands placed on present drilling operations.

Oil-based-mud (OBM) has been found to include artificial components that may be mostly alkenes, carbon monoxide (CO), and $H_2S$. Such components found in mud gas and in bottom hole samples (BHS) may be caused to occur during drilling under high stress. In at least one embodiment, the present system and method is able to determine presence of such components that can lead to uncertainties in determining natural composition underlying natural gas and oil associated with an underground formation. The uncertainties could lead to false decisions regarding formation evaluation along with false cost estimations, but can be avoided by more accurate representation of characteristics of mud gas using isotope ratios to correct a concentration of methane measured from the sample.

FIG. 1 is a schematic side view of an embodiment of a downhole drilling system 100 that includes a rig 102 and a drill string 104 coupled to the rig 102. However, other implementations of a downhole drilling system may incorporate features of a method and system disclosed herein. The drill string 104 includes a drill bit 106 at a distal end that may be rotated to engage an underground or earth formation 108 and form a wellbore 110. The drill string 104 can be formed from one or more tubulars that are mechanically coupled together (e.g., via threads, specialty couplings, or the like). As shown, the wellbore 110 includes a borehole sidewall 112 (e.g., sidewall) and an annulus 114 between the wellbore 110 and the drill string 104. Moreover, a bottom-hole assembly (BHA) 116 is positioned at the end of the drill string 104. In the example shown, the BHA is positioned at the bottom of the wellbore 110. The BHA 116 may include a drill collar 118, stabilizers 120, or the like.

In at least one embodiment, the drilling system 100 includes various tools 122, such as logging tools and surface logging tools, which may be utilized to obtain measurements from the formation 108. The logging tools, which are part of the BHA, include, for example, logging while drilling tools and may include nuclear tools, acoustic tools, seismic tools, magnetic resonance tools, resistivity tools, sampling tools, and the like. Further, computing aspects may be provided at least as discussed with respect to FIG. 5 to enable a determination of a concentration of a hydrocarbon in the underground formation based at least in part on a hydrocarbon signature in a sample and to correct the concentration of the hydrocarbon measured from the sample based at least in part on the ratio of $^{13}C$ isotopes to $^{12}C$ isotopes. The aspects in FIG. 5 may be located above ground or in a tool of the BHA. When located above ground, such aspects in FIG. 5 may be within the drill or well site, or may be at a remote facility that is other than the drill or well site.

Figure 2:
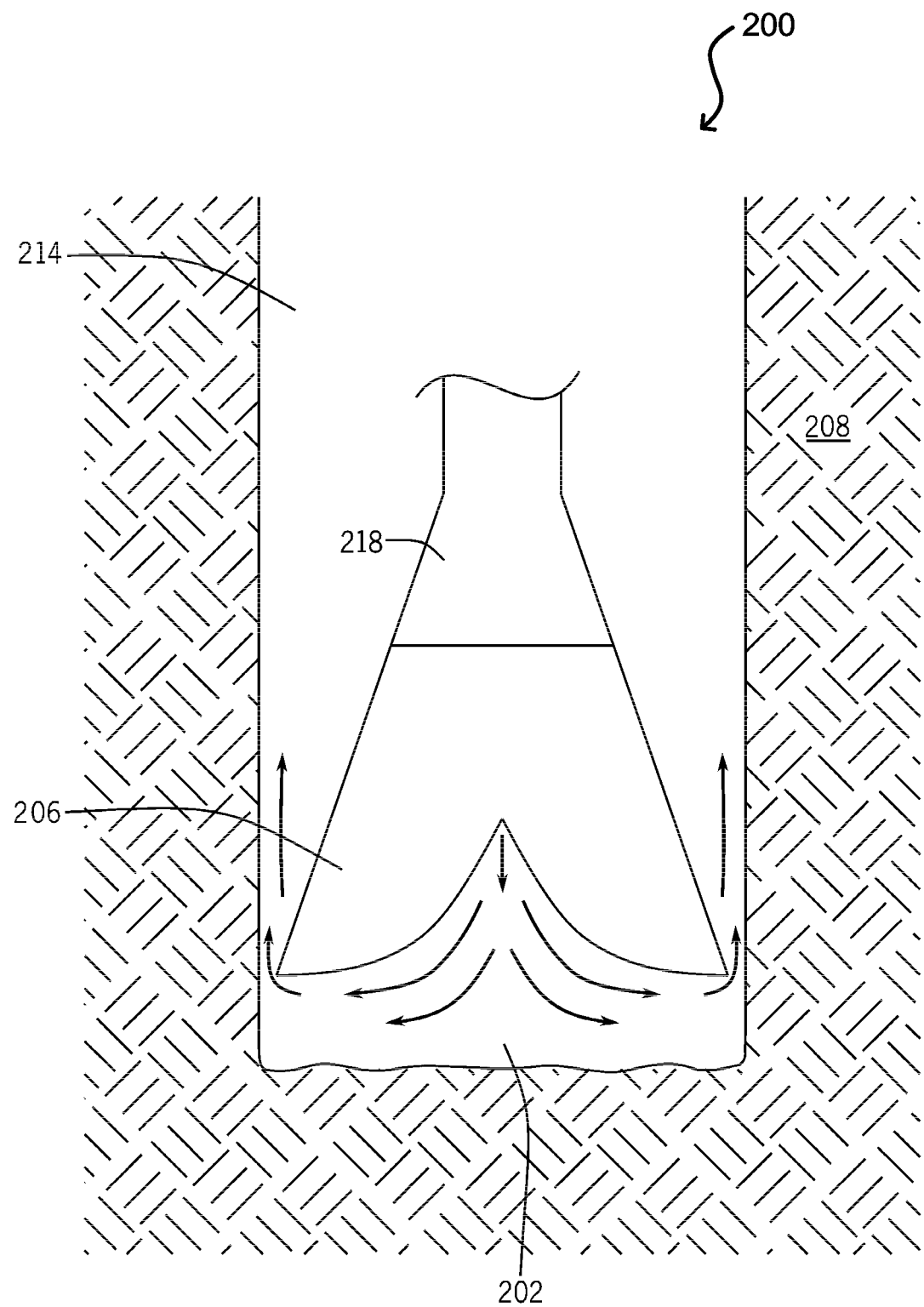
FIG. 2 illustrates an example drill bit in operation of at least one embodiment.

FIG. 2 shows a side view of an embodiment of a drilling system in operation. In operation, drilling mud or drilling fluid 202 is pumped through the drill string and out of the drill bit 206 (which may be a drill bit 106 as described in FIG. 1). The drilling mud 202 flows into the annulus 214 (which may be an annulus 114 as described in FIG. 1) and can remove cuttings from the face of the drill bit 206. Moreover, the drilling mud 202 may cool the drill bit 206 during drilling operations and provide pressure stabilization in the wellbore. As discussed in more detail below, the drilling mud 202 can be circulated upward and analyzed to determine details regarding the underground formation 208 (which may be a formation 108 as described in FIG. 1) in which drilling occurs. In other embodiments, drilling fluid is pumped downwards from outside the drilling string and then returns upwards through the drill string.

The method and system herein can use isotopic signature data of natural gases and fluids, such as (but not limited to) ethene and propene, to correct mud gas data concentrations of hydrocarbons (such as, alkane and methane), which may be affected by artificial effects. Artificial effects—beside others—can occur as a result of drill bit metamorphism (DBM), a process in which high thermal stress (such as, at temperatures that are greater than 600° C.) occurs on the drill bit 206 during drilling causes cracking of drilling material, such as fluids and gases. Such a process can introduce artifacts into the drilling mud 202. In at least one embodiment, artificial effects in mud gas may lead to a false indication of the composition of natural gases and fluids in the formation material, leading to false decisions during formation evaluation. n at least one embodiment, high thermal stress may be caused by aspects that include (but are not limited to) high weight on bit (WOB), high rate of penetration (ROP), drill-bit fatigue or overburden hook load.

Formation material (such as formation fluids, formation gases, and cuttings) enters the drilling fluid while such drilling fluid circulates through the wellbore. The formation fluids may be referred to as natural fluids or oil. Formation gases may be referred to as natural gases. Samples of the drilling fluid can be retrieved and can be analyzed (mud logging) either manually or in an automated process using the method and system described herein. During the drilling process the drilling fluid is taken uphole, to a surface area or terranean surface, and samples are taken from this drilling fluid. The analysis performed is for the composition of the drilling fluid, such as, to identify gases and fluids in the sample. Further, the analysis may also be directed to properties (such as, concentration, isotopic signature) of the components in the sample.

As the composition of the drilling mud is known before it is pumped downhole, the gas and fluid components originating from the formation fluid can be identified as distinct from the composition of the drilling mud. Such gas and fluid components are analyzed for gas type or fluid type, as well as concentration, isotopic signature, and other properties (including, reservoir fluid characterization). After the analysis, results may be displayed over time or over wellbore depth (such as, measured depth (MD) or true vertical depth (TVD)) to generate a log on formation fluid/gas properties.

In at least one embodiment, a drilling mud sample may include therein multiple samples that may be taken based at periodic drilled distances, such as, at every drilled 0.5 meters (m), 1 m, 2 m, 5 m, 10 m, or 30 m. In at least one embodiment, the samples of the drilling fluids or drilling mud may be taken time based, such as every 1 minute, every 5 minutes, 10 minutes, 30 minutes or every 60 minutes. This time is distinct from the NRT in which at least a concentration of methane is determined. The samples of the drilling fluids may correspond to different bit depths in the wellbore or different wellbore depths at these different times.

In at least one embodiment, analysis of the retrieved drilling fluid samples may take place at the well, drill, or rig site; or at a laboratory that is distinct from such sites. As the analysis is performed to generate results in NRT, including while drilling the wellbore, the wellbore trajectory may be adapted based on the results. In an example, better wellbore placement (geo-steering) and consequently higher hydrocarbon recovery may be achieved, as a result. Based at least in part on the concentration of natural methane in the drilling mud, the economic potential of a hydrocarbon reservoir in the earth formation can be estimated. In a further example, the $\delta^{13}C$ isotopic signature represents the $^{13}C/^{12}C$ isotopic abundance ratio. The concentration of hydrocarbons in the drilling fluid may be measured using a gas-chromatograph with a flame-ionization detector. Isotopic composition or fractional abundances of $^{12}C$ and $^{13}C$ may be measured using one of an isotope ratio mass spectrometer, a cavity-ring-down spectrometer, laser ablation, or an acoustic spectrometer. These components may be provided downhole or may be provided in a place where the analysis is to occur.

In at least one embodiment, drill-bit-metamorphism (DBM) may lead to enriched alkene concentrations—most over ethene, but also propene. Further, cracking at a drill bit 206 may generate shorter n-alkanes that can include altered base oil components. For example, approaches have been described using bottomhole samples (BHS) to compare with mud gas isotube data in order to estimate DMB occurrences at an end-member and to correlate DBM using C1, C2 and C3-order gases. However, such approaches may not be performed in NRT, which is a benefit offered by the present method and system, such as using a ratio of isotopes to correct a concentration of a hydrocarbon.

In at least one embodiment, a combination of datasets both from alkane and alkene hydrocarbon response in NRT at the well site supports the present method and system. The methodology herein includes estimating an amount of artificial produced methane (such as, caused due to DBM) and estimating an amount of natural formation methane. Then, isotope results for ethene and propene may be correlated with isotope values for methane within a modified Chung-Plot or other environment deliverable.

The methodology may include monitoring isotope values over time that can suggest correction to be applied to account for the artificially-produced methane values. The suggestion may be gleaned from a degree of drifting of the alkenes towards a pure cracking end-member (such as, a heavier isotope that has approximately 25-28 per mil) of an OBM. Particularly, existence of heavier isotopes suggests the drift in the alkenes and a ratio of a lighter to a heavier isotope may be used to correct a concentration of methane detected in a sample from the underground formation. In at least one embodiment, determining a ratio of $^{13}C$ isotopes to $^{12}C$ isotopes provides the $\delta^{13}C$ isotopic signatures. The ratio is determined using a concentration of each of the isotopes. A lesser correction to a hydrocarbon measure may be required when a concentration of a lighter isotope is more in a sample and a larger correction may be required when the concentration of the heavier isotope is more than the overall concentrations of isotopes in the sample. As the heavier isotope, such as the $^{13}C$ isotope, is likely indicative of a DBM, more correction may be required.

In at least one embodiment, a stable isotope and its ratio with another isotope may be expressed in a delta notation, such as ($\delta^{13}C$) per mil. A per mil is a standard reference and $\delta$ values may be calculated by $(R_{sample}/R_{standard}-1)1000$, where "R" is a ratio of a heavy to a light isotope in a sample or standard under measure. A 1:25 or 1:28 ratio, leading to the 25-28 per mil, may be in reference to a ratio of a most common isotope to a heavier isotope reference. Further, a positive $\delta$ value may imply that a sample includes more of a heavy isotope than a standard isotope of an element, while a negative $\delta$ value can imply that a sample contains less of a heavy isotope than a standard isotope of an element.

Processes that may rely solely on a presence of alkenes during drilling and that may attribute such a presence to DBM may be an inaccurate. Such a process might not be correct because a signature from a concentration variation paired with isotopic values of alkanes and alkenes may highlight aspects of whether DBM is occurring with higher confidence, and may highlight to what extent a natural underground formation has a fluid/gas pattern that is affected. As noted, these remain suggestive processes and may only focus on flagging data sets for evaluation, when alkene concentrations occur in higher concentrations. A correction of concentration and isotopic composition for methane in mud gas derived from an underground formation 208 removes such suggestions and makes accurate a process for determining not only methane concentration, but also of other hydrocarbons.

The system and method herein for correction of hydrocarbon concentration is able to significantly enhance information concerning an original value of methane in an underground formation 208, which results in improved evaluation, in NRT, of the underground formation and which can lead to less NPT and more revenue. Further, other alkanes can be corrected and inferred ratios of isotopes, derived from gas measurements and concentrations, may be used in such corrections. In addition, stable $\delta^{13}C$ isotopic signatures (and results) from mud gas compounds, such as, alkenes and alkanes, are not affected by degassing of lighter compounds to heavier ones. While this may be true for the gas itself, the isotopic signatures react differently. For example, only the pure $^{13}C$ to $^{12}C$ fractionation, inside the carbon atom may be used in determination of the ratios. Hence, using both, gas and isotope compounds, a decision of concentration of hydrocarbons is enhanced by the method and system herein. Furthermore, observed fractionation can be verified or even described in more detail using such isotope ratios.

In at least one embodiment, a system and method capable of fast alkane/alkene detection and correction using gas and isotope data could be used to adjust or to flag/log any DBM induced aspects in drilling fluids from an underground formation. The use of isotope data for at least ethane, ethene, propane, propene, methane, and $CO_2$ can be correlated and used to correct natural formation gas patterns, which can include corrections to hydrocarbon concentrations.

Figure 3A:
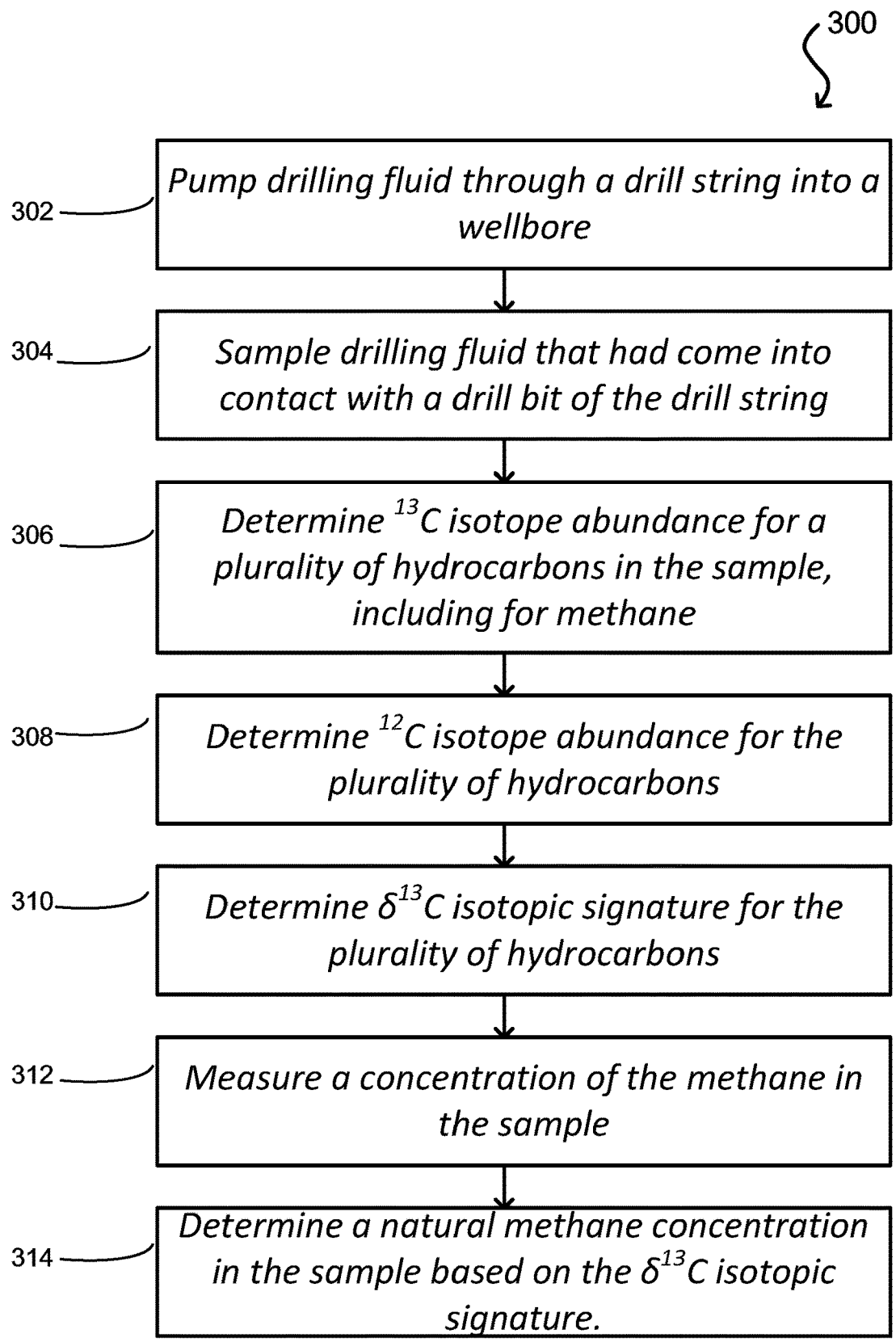
FIG. 3A illustrates an example method for determining composition of hydrocarbons in a sample of an underground formation in at least one embodiment.

FIG. 3A illustrates a method 300 for determining composition of hydrocarbons in a sample of an underground formation, in at least one embodiment. The method 300 includes a pumping step 302 for pumping drilling fluid into a well bore so that it contacts the underground formation and a sampling step 304 to take a drilling fluid sample from drilling fluid returned to a terranean surface. $^{13}C$ isotope abundance can be determined (306) for one or more hydrocarbon components in the sample of drilling fluid. The one or more hydrocarbon components can include methane, ethane, ethene, propane, propene, CO and $CO_2$. For example, $^{13}C$ isotope abundance can be determined (306) for methane, ethane, ethene, propane, and propene, among other components. Further, other hydrocarbon components than recited herein may be also subject to such a system and method for determination of concentration.

$^{12}C$ isotope abundance can be determined (308) for the same hydrocarbon components. Based on these two determinations (306, 308), a ratio of $^{13}C$ isotope abundance to $^{12}C$ isotope abundance can be determined (310, which represents a $\delta^{13}C$ isotopic signature) for the one or more hydrocarbon components in the sample of drilling fluid. A measurement (312) can be taken of a concentration of methane in the sample of drilling fluid. Based at least in part on the ratio determined in step 310, the measured methane concentration can be corrected or calculated in a determining step 314 to address the artificially-produced methane. The corrected or calculated (314) methane concentration represents the concentration of natural methane in the sample of drilling fluid.

The pumping step (302) allows drilling fluid to be pumped through a drill string into a wellbore. In at least one embodiment, the pumping step (302) for a drilling fluid may be performed by pumping the drilling fluid through a drill string and out of a drill bit into a wellbore. The pumping step 302 may also include enabling the drilling fluid to come into contact with the drill bit as the drill bit rotates in an underground formation. The drilling fluid can pass through the drill bit and lubricate the drill bit during operation.

The sampling step (304) allows sampling of the drilling fluid after it has come into contact with the drill bit so that the drilling fluid from such contact can include components not within the drilling fluid when it was initially pumped in at the pumping step 302. The drilling fluid may also include components that were not in the formation fluid when it entered the drilling fluid during the drilling process. Aspects of the sampling step 304 may be part of a mud logging feature for a wellsite. The mud logging feature includes taking the sample and performing measurements and calculations. Such measurements and calculations, including as discussed with respect to steps 306-314 may also be performed in fully automated process, including using machine learning to make inferences of an isotopic signature. As used herein, contact with the drill bit may include situations where the drilling fluid comes into proximity to the drill bit to be affected by the drill bit.

A determination step (306) is performed for $^{13}C$ isotopes (also referred to as abundance of $^{13}C$ isotopes) that can be determined for one or more hydrocarbons or hydrocarbon components in the sample of the drilling fluid. In at least one embodiment, the determining step (306) for $^{13}C$ isotope includes determining $^{13}C$ isotopes for one or more hydrocarbon components in the sample in NRT. In at least one embodiment, such a determining step (306) further includes or a separate determining step (308) may be provided for determining $^{12}C$ isotopes (also referred to as abundance of $^{12}C$ isotopes) for the one or more hydrocarbon components in the sample in NRT.

The hydrocarbon components can include methane, ethane, ethene, propane, propene, CO, and $CO_2$. In at least one embodiment, $^{13}C$ isotopes can be determined, in this step, for ethane, ethene, propane, and propene, among other components. In at least one embodiment, the one or more natural gases can be the plurality of hydrocarbons noted above, but other hydrocarbons than as listed may be also included. Particularly, in one example, other natural gases can also be used.

Based on the two determinations steps (306, 308), a further determination (310) for a ratio of $^{13}C$ isotopes to $^{12}C$ isotopes, for the sample, is performed. Such a ratio forms the $\delta^{13}C$ isotopic signatures in step 310. The determination step (310) for the ratios therefore includes determining, in near real time, a ratio of $^{13}C$ isotopes to $^{12}C$ isotopes for the one or more hydrocarbon components in the sample based at least in part on the abundance of $^{13}C$ isotopes and $^{12}C$ isotopes. Further, a measurement (312) can be taken of a concentration of the methane in the sample, as reflective of the methane concentration in the underground formation. Based at least in part on the ratio determined in step 310, the measured methane concentration can be corrected as part of the determining step (314) to arrive at a concentration of natural methane in the sample that may be representative of the natural methane in the underground formation.

Such a method (300) addresses the problems noted above where samples of drilling fluids can include artificial effects (such as, artificially-produced methane caused by artifacts like DBM) that change the natural gas component and isotopic analysis. Therefore, a method (300) as described is able to perform steps (306-314) in NRT for alkene isotope data and to correct the artificial effects that can otherwise affect determination of naturally-derived (or natural) methane at a wellsite. The drilling fluid that comes into contact with freshly crushed rock and the drill bit can be caused to circulate upward and may be sampled at a terranean surface. The sampled drilling fluid may be used in a sub-system at the well or drill site or at a remote location to determine (306-310) information about the composition of hydrocarbons in the underground formation.

According to at least one embodiment, isotopic signatures can be determined (310) for one or more natural gases in the sample in NRT. $\delta^{13}C$ isotopic signatures (representing a $^{13}C/^{12}C$ isotopic ratio) can be determined (310) for multiple hydrocarbons, including for methane, ethane, ethene, propane, and propene, among other components. After the abundance for both the $^{13}C$ isotopes and the $^{12}C$ isotopes are determined (306, 308) for each of such hydrocarbons, the $\delta^{13}C$ isotopic signatures can be determined for these hydrocarbons (310).

In addition, the concentration of natural gases, especially methane, in the underground formation can be measured (312) in NRT based on a $\delta^{13}C$ isotopic signatures of methane in the sample. Methane may occur naturally in the formation or it may be the result of artificial cracking of hydrocarbons through drill-bit metamorphism. Thus, the measurement (312) for the concentration of methane in the formation may be distorted by this artificial effect.

According to at least one embodiment, the measurement (312) for the concentration of natural methane can be determined (314) in NRT using the ratio of $^{13}C$ isotopes to $^{12}C$ isotopes for each hydrocarbon in the sample and for methane in the sample. The ratio represents the $\delta^{13}C$ isotopic signature for multiple hydrocarbons and for the methane in the sample. In at least one embodiment, at least ethane, propene, and methane are required to be in the sample for the present method and system. This ratio can also be used to estimate the extent of drill bit metamorphism, or the extent to which the operation of the drill bit cracks hydrocarbons in the drilling fluid. In at least one embodiment, the correcting feature within the determining step (314) is for the measurement of the concentration of natural methane in the underground formation is based at least in part on the ratio of $^{13}C$ isotopes to $^{12}C$ isotopes for the one or more natural gases and for methane in the sample.

According to at least one embodiment, $\delta^{13}C$ isotopic signatures for multiple natural gases can be determined in a further step of the method 300. For example, NRT determinations of $\delta^{13}C$ isotopic signatures and of concentrations can be made for ethane, ethene, propane, propene, butane, butene, butyl, and other hydrocarbons. In addition to hydrocarbons, the concentration and $\delta^{13}C$ isotopic signatures for non-hydrocarbons can be also determined. For example, the concentration and $\delta^{13}C$ isotopic signatures for $CO_2$ can be determined and compared to an expected value for such $\delta^{13}C$ isotopic signatures. The expected value may be based on the type of drill bit used and the lithology of the underground formation. The comparison of the determined signature to the expected value may provide additional information used to correct the measurement for the concentration of methane or other hydrocarbon in the underground formation.

In addition to the correction feature of the determining step (314) of hydrocarbon data, components such as hydrogen can be corrected using the carbon isotopic signature and mass balance. As such, the method 300 of FIG. 3 may be also used for non-hydrocarbons. The amount of produced hydrogen in drill bit metamorphism is equivalent to a stoichiometric ratio of participated hydrocarbons in the cracking reactions, which can be measured using the carbon isotopic signature.

As artificial effects in the mud gas may be a false indication of the composition of natural gases in the formation, the method (300) is able to determine such artificial effects and address them in NRT. For example, the presence of methane in the mud gas could be a result of methane in the formation or it could be a result of longer hydrocarbon chains cracking into methane during drill bit metamorphosis. The method (300) of FIG. 3 may be used to correct for such artifacts in the mud gas and determine the actual amount of methane and other components. Such a determination may be useful for detailed reservoir fluid characterization. Uncertainty in the actual composition of natural gas and oil in a formation ultimately leads to incorrect decisions regarding formation evaluation, along with insufficient wellbore placement and false economic forecast of the potential reservoir. The economic potential of an underground hydrocarbon reservoir may be related to the amount of hydrocarbons that can be produced from the reservoir. A parameter representing the economic potential of an underground reservoir may be the methane concentration in the reservoir.

In addition, drill bit metamorphism may lead to increased alkene concentrations in the drilling, which shows in the fluid reservoir fluid characterization. In addition, certain additional methane can result from thermal cracking of higher molecular weight hydrocarbons. This additional methane is an artificially created methane and cannot be distinguished from naturally occurring methane by surface logging analytical methods alone.

The method (300) in FIG. 3 enables distinction of the artificially created methane from natural methane present in the formation and therefore improves reservoir fluid characterization. For example, a mud gas sample may reveal a high methane concentration. However, if it is determined, that the methane reading is artificially high and that the actual amount of methane in the formation is lower, then the natural reservoir fluid may be achieved by correction made to the total methane reading. A lower gas-oil-ratio (GOR) and a potentially lower thermal maturity than estimated by mud gas analysis may be indicators of such artificially high levels of methane. The GOR is a ratio of gas volume extractable from the solution to the volume of oil at standard conditions. This information is useful for reservoir fluid characterization, basin analysis, and thus for production management, as well as for further exploration in the area.

In at least one embodiment, a combination of two or more near-real time datasets can be used in the method (300). Such datasets can include natural gas datasets, such as alkane, alkene, and/or other similar datasets. Isotope results for ethene and propene are correlated with isotope values for methane. Isotope values for $CO_2$ and CO can be added for correlation. The isotope results can be plotted, for example, in a modified Chung-plot. The isotope results can be monitored over time and the degree to which alkenes drift toward a pure cracking end-member can be used to correct for artificially-produced methane. Further, cracking through DBM can be determined based on stable carbon isotopic signatures of gas components in combination with concentrations of alkenes. For example, ongoing shifts towards the pure cracking endmember in the stable carbon isotopic signatures for methane, ethene, ethane, propene, propane, and $CO_2$, respectively, may be associated with drill bit metamorphism.

Figure 3B:
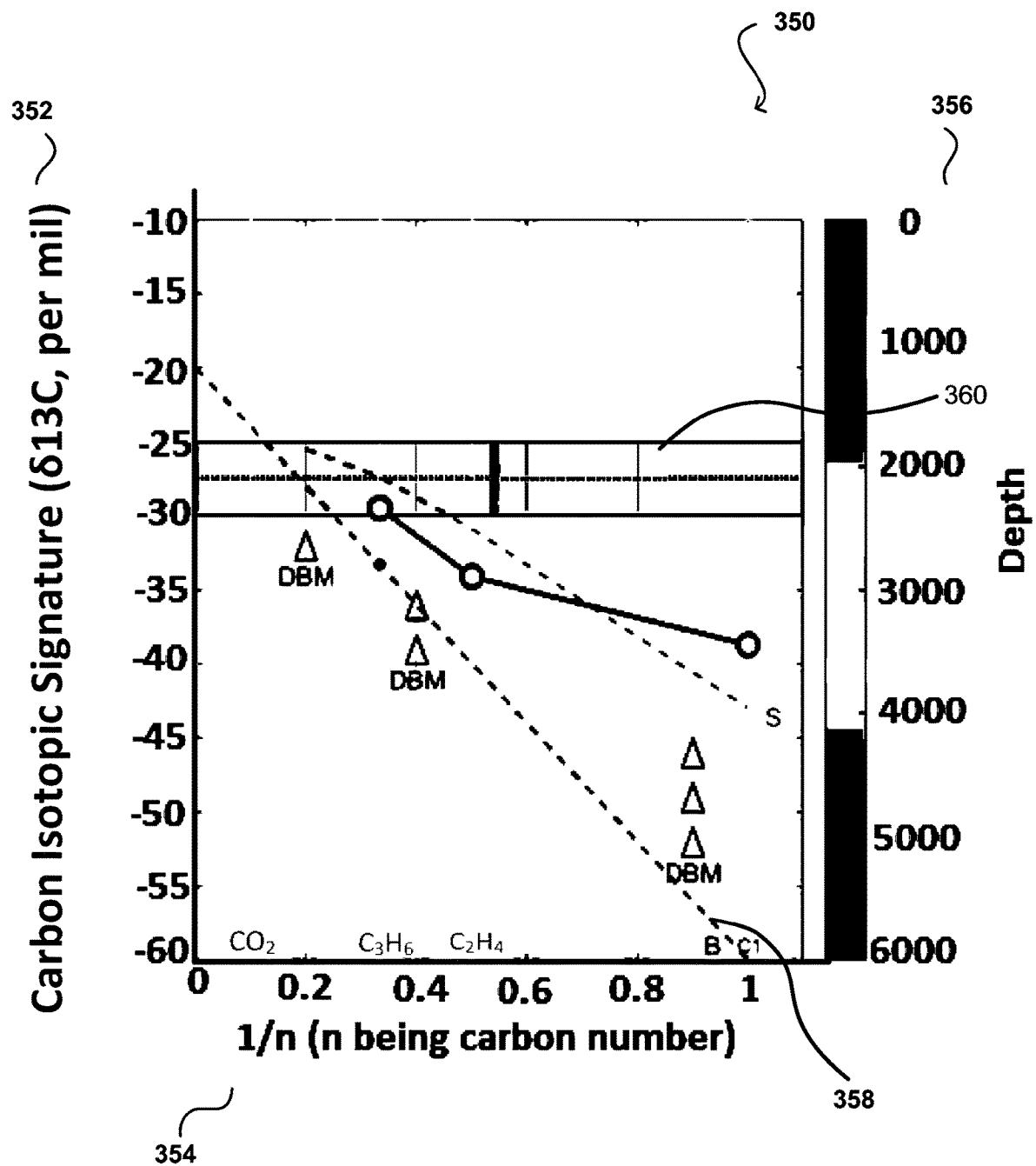
FIG. 3B illustrates a Chung Plot of a linear relationship determined between the isotopic signatures and carbon-numbers of one or more hydrocarbons in at least one embodiment.

FIG. 3B illustrates a Chung Plot 350 of a linear relationship determined between the isotopic signatures and carbon-numbers of one or more hydrocarbons in at least one embodiment. A combination of two or more datasets can be used, including natural gas data sets, such as alkane, alkene and similar datasets. Measured $\delta^{13}C$ isotopic signatures for ethene and propene are correlated with a measured $\delta^{13}C$ isotopic signature for methane. $\delta^{13}C$ isotopic signatures for non-hydrocarbons, such as, $CO_2$, CO, or $H_2S$ can be added for correlation purposes.

The appearance of CO in a sample of drilling fluid may be taken as a clear indicator for drill bit metamorphism (DBM). Further, $CO_2$ may exist in the sample as a natural $CO_2$ and as an artificially-produced $CO_2$ (such as, caused by DBM). The $\delta^{13}C$ isotopic signatures can be plotted, for example, in a modified Chung Plot, as illustrated in FIG. 3B. The modified Chung Plot is a plot of alkene isotopic signatures over carbon-number, based in part on Strąpoć and Villegas (2017) *Artificial alkenes and alkanes generated during drilling.* 28th IMOG, 17-22 Sep. 2017, Florence, Italy, which is incorporated herein by reference particularly as to discussions therein pertaining to the Chung Plot.

A classic Chung Plot plots alkane isotopic signatures over carbon-numbers. The isotopic signatures can be monitored over time and the degree to which alkenes drift toward a pure cracking end-member can be used to correct for artificially-produced methane. The measured isotopic signature of ethene, propene and further alkenes can be used to calculate the shift between a natural methane $\delta^{13}C$ isotopic signature and an encountered altered $\delta^{13}C$ isotopic signature of methane. The $\delta^{13}C$ isotopic signature of natural methane is different to the $\delta^{13}C$ isotopic signature of artificially-produced methane produced by DBM.

A linear relationship 358 is illustrated between natural, unaltered stable carbon $\delta^{13}C$ isotopic signature of alkanes 352 plotted over carbon number (C1-C3) 354 and at varying depths 356. A mathematical approach is used to correct the measured $\delta^{13}C$ isotopic signature of an alkane or other hydrocarbon (such as, for alkene) on the identification of cracking end-members, such as ethene, propene, or artificially-produced methane, where artificially-produced methane has a different $\delta^{13}C$ isotopic signature than natural methane. The mathematical approach may include an algorithm performed on a processor of a system 500 as discussed with respect to FIG. 5. The algorithm calculates a $\delta^{13}C$ isotopic signature of artificially-produced methane, which may be a result of drill bit metamorphism, and uses the $\delta^{13}C$ isotopic signature of the artificially-produced methane to correct the measured $\delta^{13}C$ isotopic signature of methane in the drilling fluid sample for the effect of drill bit metamorphism.

The algorithm can use an extrapolation based on the linear relationship 358 of isotopic signature and carbon number in the Chung Plot. The measured $\delta^{13}C$ isotopic signatures for alkenes in the sample of drilling fluid (e.g. ethene and propene) plotted over carbon number are used to fit a linear or near linear curve. Extrapolation of the linear relationship provides an extrapolated $\delta^{13}C$ isotopic signature for artificially-produced methane (carbon-number=1, C1), produced by DBM. The algorithm is able to calculate the concentration of natural methane in the sample of drilling fluid based on (i) the extrapolated $\delta^{13}C$ isotopic signature, (ii) the measured $\delta^{13}C$ isotopic signature for methane, (iii) measured concentrations of the ethene, the propene and the methane. FIG. 3B also illustrates a range 360 of typical $\delta^{13}C$ isotopic signature for base oil in an OBM to be compared with the linear relationship 358 found in part due to the DBM based artifacts.

Further, the algorithm also calculates a concentration of the artificially-produced methane in the sample of drilling fluid based on the extrapolated $\delta^{13}C$ isotopic signature. Such a calculation process in incorporated by reference herein from Schoell, M. (1980). *The Hydrogen And Carbon Isotopic Composition Of Methane From Natural Gases Of Various Origins. Geochimica et Cosmochimica Acta*, Volume 44, Issue 5, Pages 649-661. The concentration of the artificially-produced methane is used by the algorithm to calculate the concentration of the natural methane and the $\delta^{13}C$ isotopic signature of the natural methane in the sample of drilling fluid.

The concentration of natural methane in the drilling fluid can be used to estimate the amount of natural methane in the earth formation, corresponding to step 314 in FIG. 3A. The mathematical method, as explored for methane herein, may be used for any other kind of hydrocarbon component affected by DBM. The algorithm may calculate the extrapolated $\delta^{13}C$ isotopic signature based on the mathematical dependencies between $\delta^{13}C$ isotopic signature and carbon number, which is also described in Strąpoć (2017) and incorporated herein by reference. The mathematical approach does not necessarily require a plot (a graph) to determine the extrapolated $\delta^{13}C$ isotopic signature, the algorithm in the mathematical approach can perform the extrapolation within the software code executed by a processor without generating a plot in each iteration where such algorithm is executed.

In at least one embodiment, a signature from a concentration variation may be paired with isotopic signature values of alkanes and alkenes that can be used to determine to what extent the natural formation fluid/gas pattern is affected by DBM. In at least one embodiment, stable and comparable datasets of isotopes (such as, $^{13}C$ isotopes) are provided, such that isotopic signatures can be determined at the rig site or in the laboratory, in NRT. Measured methane concentrations, or the concentrations of other carbon containing drilling fluid components, can then be corrected to the real natural formation values (such as, natural methane) by using correlated isotope results for natural gases, including alkenes, alkanes and similar datasets. The corrected data can then be used to evaluate the formation fluid.

In at least one embodiment, isotopic signatures may be provided in NRT or post-well site NRT. Particularly, the NRT is determined from when the sample is entered for the determination of the $\delta^{13}C$ isotopic signatures till a step of performing the correcting of the concentration of methane is completed. Such an NRT is 30 minutes or less, and so such a method may be applied at a well or drill site or may be applied to a sample post-well site.

There are several ways to determine the confidence of the NRT. For example, the signatures can be compared to expected signatures for certain components that are expected to be present in the drilling fluid based on the type of drill bit used. The degree to which the measured isotopic signatures or concentration signatures align with the expected isotopic signatures or concentration signatures can be used to determine the confidence level for other measured signatures.

In at least one embodiment, diamond bits, particularly when used in anhydrite, gypsum, or dolomite formations, may result in increased levels of CO and/or $CO_2$ concentrations in the sample of drilling fluid. By measuring CO, $CO_2$, and by comparing the measured values against values expected based on the drill bit and formation type, the isotopic signatures of hydrocarbons can be determined with greater confidence. In one example, a $\delta^{13}C$ isotopic signature is a function of chemical composition of the drilling fluid and the concentration of $CO_2$ generated by drill bit metamorphism. The calculation of the natural methane concentration in the sample of drilling fluid may be improved by accounting for biodegradation. That is, the shift of the $\delta^{13}C$ isotopic signature of the measured methane in the sample of drilling fluid may not only be affected by drill bit metamorphism, but also by biodegradation. As such, the $\delta^{13}C$ isotopic signature of $CO_2$ may be used to estimate the amount of shift of the $\delta^{13}C$ isotopic signature of the methane in the drilling sample. Further, correlating the change of the $\delta^{13}C$ isotopic signature of the $CO_2$ with varying $CO_2$ concentration and the change of the $\delta^{13}C$ isotopic signature of ethene with varying ethene concentration allows for calculation of a contribution of biodegradation to the shift of the $\delta^{13}C$ isotopic signature.

Figure 4:
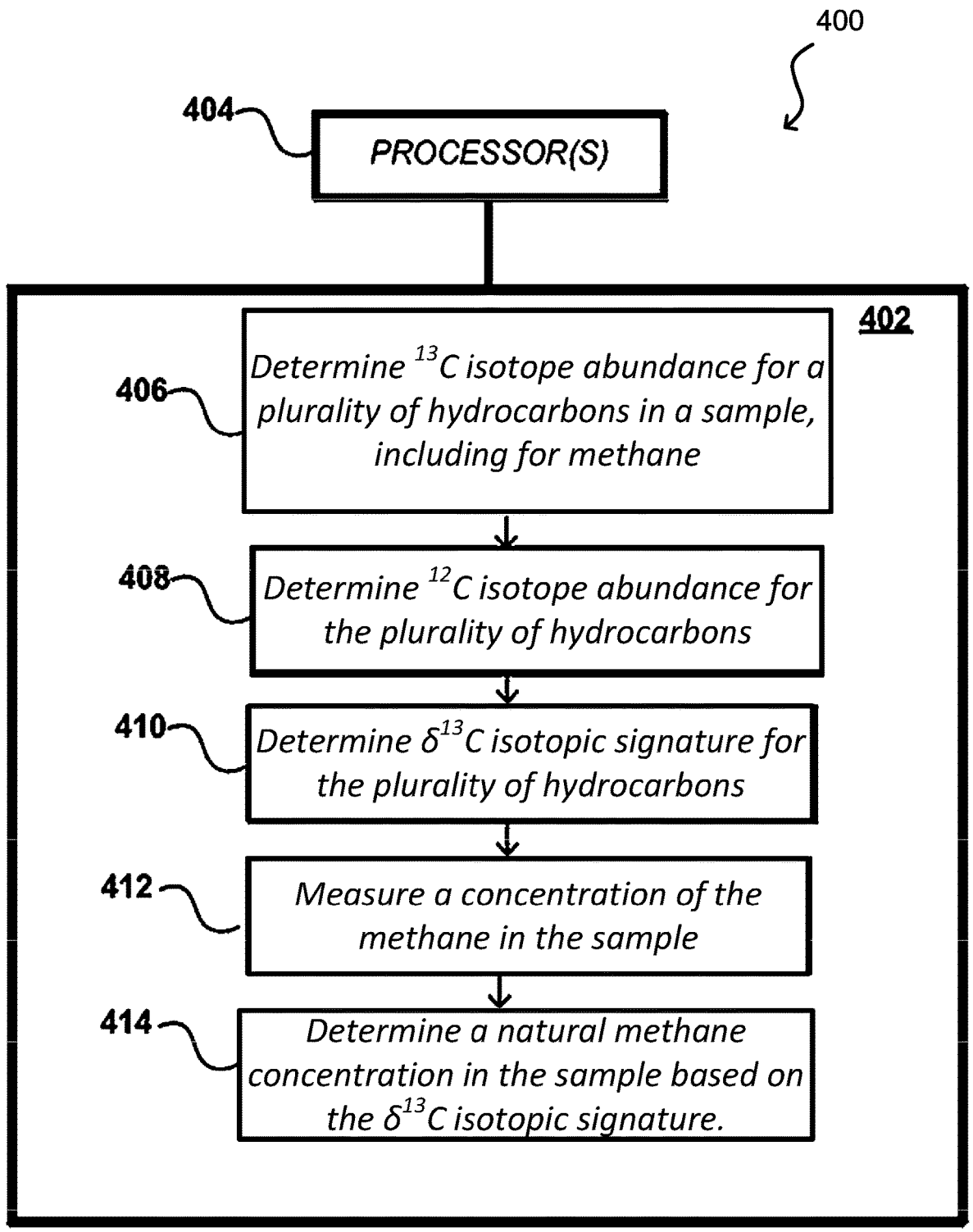
FIG. 4 illustrates an example system for determining a composition of hydrocarbons in a sample of an underground formation, in at least one embodiment.

FIG. 4 illustrates an example system 400 that can be used to determine the composition of natural methane in a sample of an underground formation. The system 400 can include memory 402 with instructions that, when executed by one or more processors 404, cause the system 400 to execute a number of steps (406-414). For example, the instructions can include determining (406) $^{13}C$ isotope abundance for one or more natural gas components, including for methane, in the sample in near real time. In at least one embodiment, the one or more natural gas components can be the plurality of hydrocarbons including methane and other hydrocarbons discussed throughout herein.

$^{12}C$ isotope abundance can be determined (408) in near real time for the same components. Based on these two determinations (406, 408), the ratio of $^{12}C$ isotopes to $^{13}C$ isotopes can be determined (410), as the $\delta^{13}C$ isotopic signature, for each of the plurality of hydrocarbons in the sample. The instructions can further include measuring (412) a concentration of methane in the sample that may be reflective of a methane concentration n the underground formation. Based at least in part on the ratio determined in step 410, the measured methane concentration can be corrected (414) for removing artificially-produced methane so that the corrected methane concentration represents the concentration of natural methane in the sample of drilling fluid.

In at least one embodiment, a neural network or other machine learning algorithm may be enabled to receive isotopic signatures and may be trained to use the isotopic signatures or to use scales (such as, ratios) associated with the isotopic signatures to infer a correction to be made to the methane or other hydrocarbon concentration from a wellsite. In at least one embodiment, the neural network or machine learning algorithm may be trained to infer a methane or other hydrocarbon concentration if the correction may be correlated with a ratio of the isotopic signatures.

Figure 5:
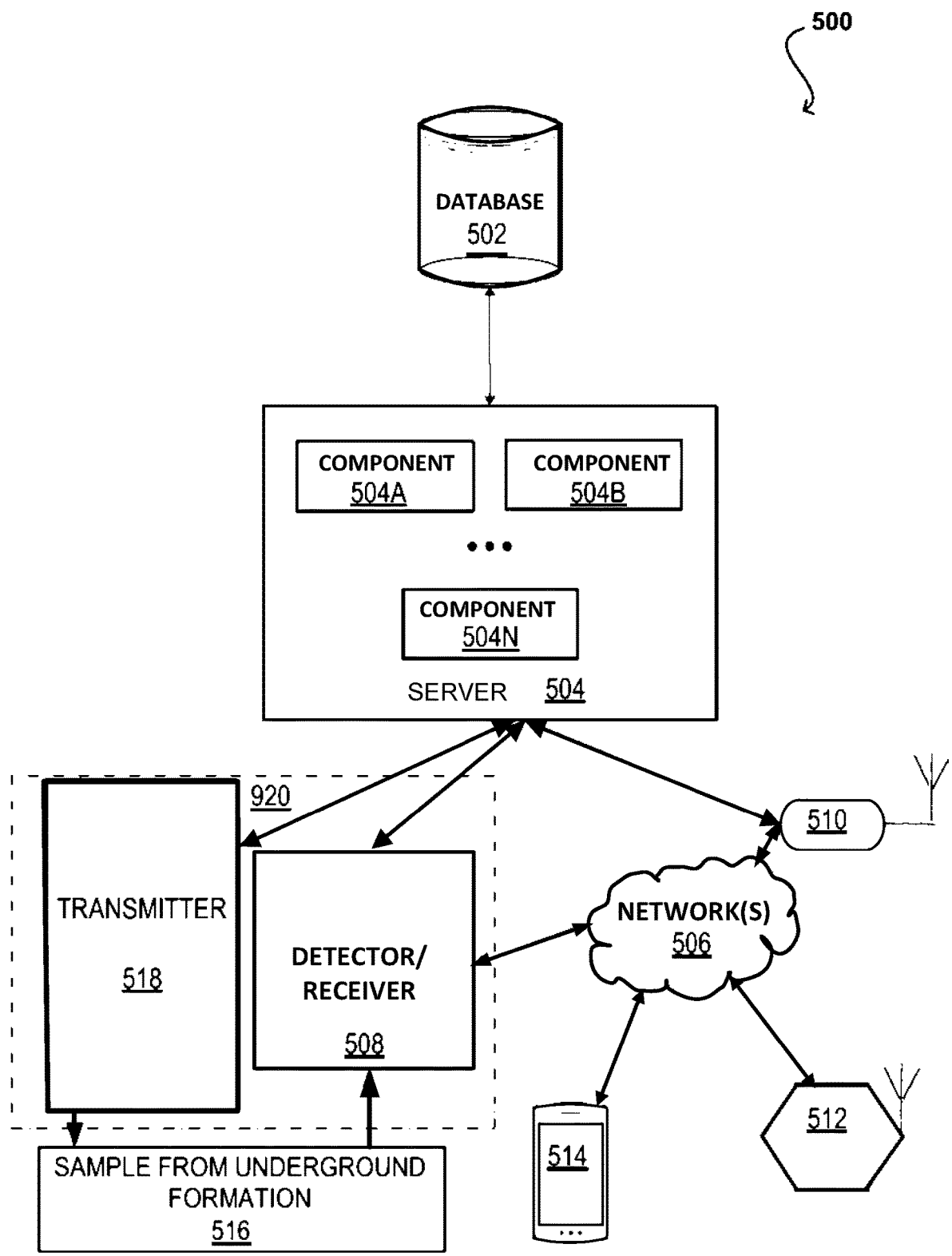
FIG. 5 illustrates computer and network aspects for a system to be used with a method for determining a hydrocarbon concentration from formation fluid, according to at least one embodiment.

In at least one embodiment, computer and network aspects 500 may be used with a downhole system as illustrated in FIG. 5, may be used as described herein. In at least one embodiment, these computer and network aspects 500 may include a distributed system. In at least one embodiment, a distributed system 500 may include one or more computing devices 512, 514. In at least one embodiment, one or more computing devices 512, 514 may be adapted to execute and function with a client application, such as with browsers or a stand-alone application, and are adapted to execute and function over one or more network(s) 506.

In at least one embodiment, a server 504, having components 504A-N may be communicatively coupled with computing devices 512, 514 via network 506 and via a receiver device 508, if provided. In at least one embodiment, components 512, 514 include processors, memory and random-access memory (RAM). In at least one embodiment, server 504 may be adapted to operate services or applications to manage functions and sessions associated with database access 502 and associated with computing devices 512, 514. In at least one embodiment, server 504 may be associated with a receiver or detector device 508 of a tool 520.

In at least one embodiment, server 504 may be at a wellsite location, but may also be at a distinct location from a wellsite location. In at least one embodiment, such a server 504 may support or be associated with a tool 520 (such as, one of tools 122 described in connection with FIG. 1 or a tool that is a surface logging tool and that is not in a downhole environment). Such a tool 920 may include a spectrometer, a gas chromatograph, and/or other appropriate detection system for measuring isotopes and gas concentrations, and for detecting signatures of one or more gasses. A transmitter 518 provides signals or waves to a sample from an underground formation 516. The drilling fluid from an underground formation 516 may be mud gas circulated out of a downhole environment after contacting a drill bit and the underground formation, and from which a sample is secured at a terranean surface. The receiver or detector device 508 of the tool 520 can receive one or more returned or reflected signals or waves.

In at least one embodiment, a system for determining a hydrocarbon concentration may include aspects that are adapted to transmit, either through wires or wirelessly, information received therein, from a detector or a receiver back to the surface. In at least one embodiment, such information may be received in a receiver device and transmitted from there. In at least one embodiment, a server 504 may function as a detector or receiver device but may also perform other functions. In at least one embodiment, one or more component 504A-N may be adapted to function as a detector or receiver device within a server 504. In at least one embodiment, one or more components 504A-N may include one or more processors and one or more memory devices adapted to function as a detector or receiver device, while other processors and memory devices in server 504 may perform other functions.

In at least one embodiment, a server 504 may also provide services or applications that are software-based in a virtual or a physical environment. In at least one embodiment, when server 504 is a virtual environment, then components 504A-N are software components that may be implemented on a cloud. In at least one embodiment, this feature allows remote operation of a system for determining a hydrocarbon concentration using a tool, as discussed at least in reference to FIGS. 1-4. In at least one embodiment, this feature also allows for remote access to information received and communicated between any of aforementioned devices. In at least one embodiment, one or more components 504A-N of a server 504 may be implemented in hardware or firmware, other than a software implementation described throughout herein. In at least one embodiment, combinations thereof may also be used.

In at least one embodiment, one computing device 510-514 may be a smart monitor or a display having at least a microcontroller and memory having instructions to enable display of information monitored by a detector or receiver device. In at least one embodiment, one computing device 510-512 may be a transmitter device to transmit directly to a receiver device or to transmit via a network 506 to a receiver device 508 and to a server 504, as well as to other computing devices 512, 514.

In at least one embodiment, other computing devices 512, 514 may include portable handheld devices that are not limited to smartphones, cellular telephones, tablet computers, personal digital assistants (PDAs), and wearable devices (head mounted displays, watches, etc.). In at least one embodiment, other computing devices 512, 514 may operate one or more operating systems including Microsoft Windows Mobile®, Windows® (of any generation), and/or a variety of mobile operating systems such as iOS®, Windows Phone®, Android®, BlackBerry®, Palm OS®, and/or variations thereof.

In at least one embodiment, other computing devices 512, 514 may support applications designed as internet-related applications, electronic mail (email), short or multimedia message service (SMS or MMS) applications and may use other communication protocols. In at least one embodiment, other computing devices 512, 514 may also include general purpose personal computers and/or laptop computers running such operating systems as Microsoft Windows®, Apple Macintosh®, and/or Linux®. In at least one embodiment, other computing devices 512, 514 may be workstations running UNIX® or UNIX-like operating systems or other GNU/Linux operating systems, such as Google Chrome OS®. In at least one embodiment, thin-client devices, including gaming systems (Microsoft Xbox®) may be used as other computing device 512, 514.

In at least one embodiment, network(s) 506 may be any type of network that can support data communications using various protocols, including TCP/IP (transmission control protocol/Internet protocol), SNA (systems network architecture), IPX (Internet packet exchange), AppleTalk®, and/or variations thereof. In at least one embodiment, network(s) 506 may be a networks that is based on Ethernet, Token-Ring, a wide-area network, Internet, a virtual network, a virtual private network (VPN), a local area network (LAN), an intranet, an extranet, a public switched telephone network (PSTN), an infra-red network, a wireless network (such as that operating with guidelines from an institution like the Institute of Electrical and Electronics (IEEE) 802.11 suite of protocols, Bluetooth®, and/or any other wireless protocol), and/or any combination of these and/or other networks.

In at least one embodiment, a server 504 runs a suitable operating system, including any of operating systems described throughout herein. In at least one embodiment, server 504 may also run some server applications, including HTTP (hypertext transport protocol) servers, FTP (file transfer protocol) servers, CGI (common gateway interface) servers, JAVA® servers, database servers, and/or variations thereof. In at least one embodiment, a database 502 is supported by database server feature of a server 504 provided with front-end capabilities. In at least one embodiment, such database server features include those available from Oracle®, Microsoft®, Sybase®, IBM® (International Business Machines), and/or variations thereof.

In at least one embodiment, a server 504 is able to provide feeds and/or real-time updates for media feeds. In at least one embodiment, a server 504 is part of multiple server boxes spread over an area, but functioning for a presently described process for fast in-field chromatography. In at least one embodiment, server 504 includes applications to measure network performance by network monitoring and traffic management. In at least one embodiment, a provided database 502 enables information storage from a wellsite, including user interactions, usage patterns information, adaptation rules information, and other information.

In some embodiments, the relationships between variance values and corresponding characteristics or status of components of well structure may be established through historical data or lab-generated data. This information may take the form of an index or algorithm. In some embodiments, a machine learning approach may be utilized in which training data includes known variance values and corresponding well structure status. An input of new variance values can produce predicted well structure status information based on the machine learning model trained on such data.

It should be appreciated that embodiments herein may utilize one or more values that may be experimentally determined or correlated to certain performance characteristics based on operating conditions under similar or different conditions. The present disclosure described herein, therefore, is well adapted to carry out the objects and attain the ends and advantages mentioned, as well as others inherent therein. While a presently preferred embodiment of the disclosure has been given for purposes of disclosure, numerous changes exist in the details of procedures for accomplishing the desired results. These and other similar modifications will readily suggest themselves to those skilled in the art and are intended to be encompassed within the spirit of the present disclosure disclosed herein and the scope of the appended claims.

While techniques herein may be subject to modifications and alternative constructions, these variations are within spirit of present disclosure. As such, certain illustrated embodiments are shown in drawings and have been described above in detail, but these are not limiting disclosure to specific form or forms disclosed; and instead, cover all modifications, alternative constructions, and equivalents falling within spirit and scope of disclosure, as defined in appended claims.

Terms such as a, an, the, and similar referents, in context of describing disclosed embodiments (especially in context of following claims), are understood to cover both singular and plural, unless otherwise indicated herein or clearly contradicted by context, and not as a definition of a term. Including, having, including, and containing are understood to be open-ended terms (meaning a phrase such as, including, but not limited to) unless otherwise noted. Connected, when unmodified and referring to physical connections, may be understood as partly or wholly contained within, attached to, or joined together, even if there is something intervening.

Recitation of ranges of values herein are merely intended to serve as a shorthand method of referring individually to each separate value falling within range, unless otherwise indicated herein and each separate value is incorporated into specification as if it were individually recited herein. In at least one embodiment, use of a term, such as a set (for a set of items) or subset unless otherwise noted or contradicted by context, is understood to be nonempty collection including one or more members. Further, unless otherwise noted or contradicted by context, term subset of a corresponding set does not necessarily denote a proper subset of corresponding set, but subset and corresponding set may be equal.

Conjunctive language, such as phrases of form, at least one of A, B, and C, or at least one of A, B and C, unless specifically stated otherwise or otherwise clearly contradicted by context, is otherwise understood with context as used in general to present that an item, term, etc., may be either A or B or C, or any nonempty subset of set of A and B and C. In at least one embodiment of a set having three members, conjunctive phrases, such as at least one of A, B, and C and at least one of A, B and C refer to any of following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, terms such as plurality, indicates a state of being plural (such as, a plurality of items indicates multiple items). In at least one embodiment, a number of items in a plurality is at least two, but can be more when so indicated either explicitly or by context. Further, unless stated otherwise or otherwise clear from context, phrases such as based on means based at least in part on and not based solely on.

Operations of a method 300 or sub-steps described herein can be performed in any suitable order unless otherwise indicated herein or otherwise clearly contradicted by context. In at least one embodiment, a method includes processes such as those processes described herein (or variations and/or combinations thereof) that may be performed under control of one or more computer systems configured with executable instructions and that may be implemented as code (e.g., executable instructions, one or more computer programs or one or more applications) executing collectively or exclusively on one or more processors, by hardware or combinations thereof.

In at least one embodiment, such code may be stored on a computer-readable storage medium. In at least one embodiment, such code may be a computer program having instructions executable by one or more processors. In at least one embodiment, a computer-readable storage medium is a non-transitory computer-readable storage medium that excludes transitory signals (such as a propagating transient electric or electromagnetic transmission) but includes non-transitory data storage circuitry (such as buffers, cache, and queues) within transceivers of transitory signals. In at least one embodiment, code (such as executable code or source code) is stored on a set of one or more non-transitory computer-readable storage media having stored thereon executable instructions (or other memory to store executable instructions) that, when executed (such as a result of being executed) by one or more processors of a computer system, cause computer system to perform operations described herein.

In at least one embodiment, a set of non-transitory computer-readable storage media includes multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors—in at least one embodiment, a non-transitory computer-readable storage medium store instructions and a main central processing unit (CPU) executes some of instructions while other processing units execute other instructions. In at least one embodiment, different components of a computer system have separate processors and different processors execute different subsets of instructions.

In at least one embodiment, computer systems are configured to implement one or more services that singly or collectively perform operations of processes described herein and such computer systems are configured with applicable hardware and/or software that enable performance of operations. In at least one embodiment, a computer system that implements at least one embodiment of present disclosure is a single device or is a distributed computer system having multiple devices that operate differently such that distributed computer system performs operations described herein and such that a single device does not perform all operations.

In at least one embodiment, even though the above discussion provides at least one embodiment having implementations of described techniques, other architectures may be used to implement described functionality, and are intended to be within scope of this disclosure. In addition, although specific responsibilities may be distributed to components and processes, they are defined above for purposes of discussion, and various functions and responsibilities might be distributed and divided in different ways, depending on circumstances.

In at least one embodiment, although subject matter has been described in language specific to structures and/or methods or processes, it is to be understood that subject matter claimed in appended claims is not limited to specific structures or methods described. Instead, specific structures or methods are disclosed as example forms of how a claim may be implemented.

From all the above, a person of ordinary skill would readily understand that the tool of the present disclosure provides numerous technical and commercial advantages, and can be used in a variety of applications. Various embodiments may be combined or modified based in part on the present disclosure, which is readily understood to support such combination and modifications to achieve the benefits described above.

The invention claimed is:

1. A method to measure a concentration of natural methane in a sample of drilling fluid, the method comprising:
pumping the drilling fluid through a drill string into a wellbore;
taking the sample of the drilling fluid to a terranean surface, the sample comprising a first hydrocarbon component, a second hydrocarbon component, and methane, the methane comprising the natural methane originating from an earth formation and artificially-produced methane caused by drill bit metamorphism;
determining a $\delta^{13}C$ isotopic signature of the first hydrocarbon component in the sample;
determining a $\delta^{13}C$ isotopic signature of the second hydrocarbon component in the sample;
determining a $\delta^{13}C$ isotopic signature of the methane in the sample; and
determining, using a processor, the concentration of the natural methane in the sample based in part on the $\delta^{13}C$ isotopic signature of the first hydrocarbon component, the $\delta^{13}C$ isotopic signature of the second hydrocarbon component, and the $\delta^{13}C$ isotopic signature of the methane.

2. The method of claim 1, wherein the first hydrocarbon component and the second hydrocarbon component are alkenes.

3. The method of claim 1, wherein the first hydrocarbon component is ethene.

4. The method of claim 1, wherein the second hydrocarbon component is propene.

5. The method of claim 1, wherein the steps of taking the sample and determining of the $\delta^{13}C$ isotopic signature of the methane is performed while drilling the wellbore.

6. The method of claim 1, further comprising:
determining a linear relationship between the $\delta^{13}C$ isotopic signature of the first hydrocarbon component and the $\delta^{13}C$ isotopic signature of the second hydrocarbon component, the linear relationship based in part on the carbon number of the first hydrocarbon component and the carbon number of the second hydrocarbon component.

7. The method of claim 6, wherein the determining of the concentration of the natural methane comprises an extrapolation of the linear relationship to provide a $\delta^{13}C$ isotopic signature of a hydrocarbon component with a carbon number that is equal to 1.

8. The method of claim 1, further comprising changing a trajectory of the wellbore based on the determined concentration of the natural methane.

9. The method of claim 1, further comprising:
determining a parameter representing an economic potential of an underground hydrocarbon reservoir that at least partially incorporates the wellbore, the economic potential based at least in part on the concentration of the natural methane.

10. The method of claim 1, wherein the sample of the drilling fluid comprises a plurality of samples, at least two samples of the plurality of samples correspond to different depths of the wellbore.

11. The method of claim 1, further comprising:
determining a $\delta^{13}C$ isotopic signature of carbon dioxide (CO2); and
determining the concentration of the natural methane based in part on the $\delta^{13}C$ isotopic signature of CO2.

12. The method of claim 1, further comprising:
measuring, using the sample, a first concentration of the first hydrocarbon component, a second concentration of the second hydrocarbon component and a third concentration of the methane, wherein the determined concentration of the natural methane in the sample is based on the $\delta^{13}C$ isotopic signature of the first hydrocarbon component, the $\delta^{13}C$ isotopic signature of the second hydrocarbon component, the $\delta^{13}C$ isotopic signature of the methane, the first concentration, the second concentration, and the third concentration.

13. A method to measure a concentration of natural methane in a sample of drilling fluid, the method comprising:
determining a $\delta^{13}C$ isotopic signature of a first hydrocarbon component in the sample;
determining a $\delta^{13}C$ isotopic signature of a second hydrocarbon component in the sample;
determining a $\delta^{13}C$ isotopic signature of methane in the sample, the methane comprising the natural methane originating from an earth formation and artificially-produced methane caused by drill bit metamorphism; and
determining, using a processor, the concentration of the natural methane in the sample based on the $\delta^{13}C$ isotopic signature of the first hydrocarbon component, the $\delta^{13}C$ isotopic signature of the second hydrocarbon component, and the $\delta^{13}C$ isotopic signature of the methane.

14. The method of claim 13, wherein the first hydrocarbon component and the second hydrocarbon component are alkenes.

15. The method of claim 13, wherein the first hydrocarbon component is ethene.

16. The method of claim 13, wherein the second hydrocarbon component is propene.

17. The method of claim 13, further comprising:
determining a $\delta^{13}C$ isotopic signature of carbon dioxide (CO2); and
determining the concentration of the natural methane using the $\delta^{13}C$ isotopic signature of CO2.

18. A system to measure a concentration of natural methane in a sample of drilling fluid, the system comprising:
at least one processor; and
a memory including instructions that, when executed by the at least one processor, cause the system to:
determine a $\delta^{13}C$ isotopic signature of a first hydrocarbon component in the sample;
determine a $\delta^{13}C$ isotopic signature of a second hydrocarbon component in the sample;
determine a $\delta^{13}C$ isotopic signature of methane in the sample, the methane comprising the natural methane originating from an earth formation and artificially-produced methane caused by drill bit metamorphism; and determine the concentration of the natural methane in the sample based on the $\delta^{13}C$ isotopic signature of the first hydrocarbon component, the $\delta^{13}C$ isotopic signature of the second hydrocarbon component, and the $\delta^{13}C$ isotopic signature of the methane.

19. The system of claim 18, further comprising a gas chromatograph to determine a concentration of at least the methane in the sample.

20. The system of claim 18, further comprising a mass spectrometer to perform the determination of the $\delta^{13}C$ isotopic signature of the first hydrocarbon component, the $\delta^{13}C$ isotopic signature of the second hydrocarbon component, and the $\delta13C$ isotopic signature of the methane.

\* \* \* \* \*